US007479490B2

(12) United States Patent
Adams et al.

(10) Patent No.: US 7,479,490 B2

(45) Date of Patent: Jan. 20, 2009

(54) PELLET FOR A PRESURRIZED PIPELINE

(75) Inventors: Robert R. Adams, Sugar Grove, IL (US); Rodney H. Banks, Aurora, IL (US); Mita Chattoraj, Warrenville, IL (US); Joe L. Schwartz, Aurora, IL (US)

(73) Assignee: Nalco Company, Naperville, IL (US)

( * ) Notice: Subject to any disclaimer, the term of this patent is extended or adjusted under 35 U.S.C. 154(b) by 724 days.

(21) Appl. No.: 11/055,206

(22) Filed: Feb. 10, 2005

(65) Prior Publication Data

US 2005/0133091 A1 Jun. 23, 2005

Related U.S. Application Data

(62) Division of application No. 10/674,856, filed on Sep. 30, 2003, now Pat. No. 6,901,945.

(51) Int. Cl.

*A61K 9/14* (2006.01)
*A61K 31/536* (2006.01)
*A61K 47/00* (2006.01)

(52) U.S. Cl. .................... 514/229.8; 424/489; 424/502; 514/769; 514/772

(58) Field of Classification Search ....................... None
See application file for complete search history.

(56) References Cited

U.S. PATENT DOCUMENTS

| | | | |
|---|---|---|---|
| 2,657,805 | A | 11/1953 | Paleer |
| 3,353,723 | A | 11/1967 | Wieleba |
| 4,058,240 | A | 11/1977 | Becker |
| 4,357,953 | A | 11/1982 | Patterson |
| 4,687,381 | A | 8/1987 | Dumain et al. |
| 4,828,145 | A | 5/1989 | Raufast |
| 4,977,921 | A | 12/1990 | Knight et al. |
| 6,314,979 | B1 | 11/2001 | Lips |
| 6,329,165 | B1 | 12/2001 | Chattoraj et al. |

*Primary Examiner*—Johann R Richter
*Assistant Examiner*—Frank I Choi
(74) *Attorney, Agent, or Firm*—Peter A. DiMattia; Michael B. Martin

(57) ABSTRACT

A system of equipment allowing addition of solid materials to a pressurized pipeline wherein said solid material is conveyed in such a way as to be readily dissolved by the liquid in said pipeline. The system includes a solid material transfer device that is used to transfer solid material to the point of intake in a pressurized pipeline, without allowing liquid from the process pipeline to access the solid material in the solid material feeder. The system of equipment has been found to be particularly useful in feeding pellets containing resazurin.

3 Claims, 7 Drawing Sheets

PELLET FOR A PRESURRIZED PIPELINE

CROSS-REFERENCE TO RELATED APPLICATION

This application is a divisional application of application Ser. No. 10/674,856 filed on Sep. 30, 2003 now U.S. Pat. No. 6,901,945.

FIELD OF THE INVENTION

This invention relates generally to a system of equipment and methods of using same for addition of solid materials to a pipeline.

BACKGROUND OF THE INVENTION

Different types of equipment to add materials to pressurized pipelines are known in the art of materials handling. Some of this equipment is commercially available while others of this type of equipment exist only in laboratory and pilot plant operations.

See U.S. Pat. No. 3,353,723 which describes and claims a rotary valve for batching and charging loose materials, for instance granular, chipped or otherwise comminuted substances, into a container under internal pressure.

Also see U.S. Pat. No. 4,828,145 which describes and claims a rotary-type metering device making it possible to dispense granular substances consisting of fine particles which are difficult to handle. The metering device consists of a spherical core rotating around a horizontal axis inside a casing comprising a feed orifice and an outlet orifice.

Also see U.S. Pat. No. 4,687,381 which describes and claims a device and process for introducing a powder with catalytic activity into a fluidized bed polymerization reactor.

When the pressurized liquid is compressed air, a reference describing an automatic drain system is U.S. Pat. No. 4,058,240 which describes an automatic drain system for compressed air systems, air dryers, aftercoolers, separators and the like, which eliminates the loss of compressed air and is not clogged by sediment in the accumulated liquid or slurry.

It would be desirable to have a system of equipment that provided for the addition of solid materials to a pipeline, that also provided for optimal contact of the solid material with the liquid in the pipeline and also permitted addition of solid materials to a pressurized pipeline.

SUMMARY OF THE INVENTION

The first aspect of the instant claimed invention is a system of equipment allowing addition of solid materials to a pressurized pipeline wherein said solid material is conveyed in such a way as to be readily dissolved by the liquid in said pipeline, comprising:

(a) a solid material storage container linked with a solid material feeder;

(b) solid material feeder pipe to convey said solid material from said solid material feeder to a solid material transfer device;

(c) a solid material transfer device used to transfer said solid material from said solid material feeder pipe to the point of intake in the process pipeline, without allowing liquid from the process pipeline to access the solid material in the solid material feeder; and (d) means for holding said solid material in place for a sufficient length of time such that the liquid in said process pipeline can contact and dissolve said solid material downstream of the point of intake in the process pipeline.

The second aspect of the instant claimed invention is a pellet comprising:

a) from about 1 to about 40 weight percent resazurin;

b) from about 0 to about 30 weight percent anhydrous sodium sulfate;

c) from about 15 to about 60 weight percent 1-hydroxyethylidene biphosphonate, tetrasodium salt; and d) from about 0.0 to about 4.0 weight percent stearate.

DETAILED DESCRIPTION OF THE INVENTION

The instant claimed invention is a system of equipment allowing addition of solid materials to a pressurized pipeline wherein said solid material is conveyed in such a way as to be readily dissolved by the liquid in said pipeline, comprising:

(a) a solid material storage container linked with a solid material feeder;

(b) solid material feeder pipe to convey said solid material from said solid material feeder to a solid material transfer device;

(c) a solid material transfer device used to transfer said solid material from said solid material feeder pipe to the point of intake in the process pipeline, without allowing liquid from the process pipeline to access the solid material in the solid material feeder; and (d) means for holding said solid material in place for a sufficient length of time such that the liquid in said process pipeline can contact and dissolve said solid material downstream of the point of intake in the process pipeline.

Figure 1:
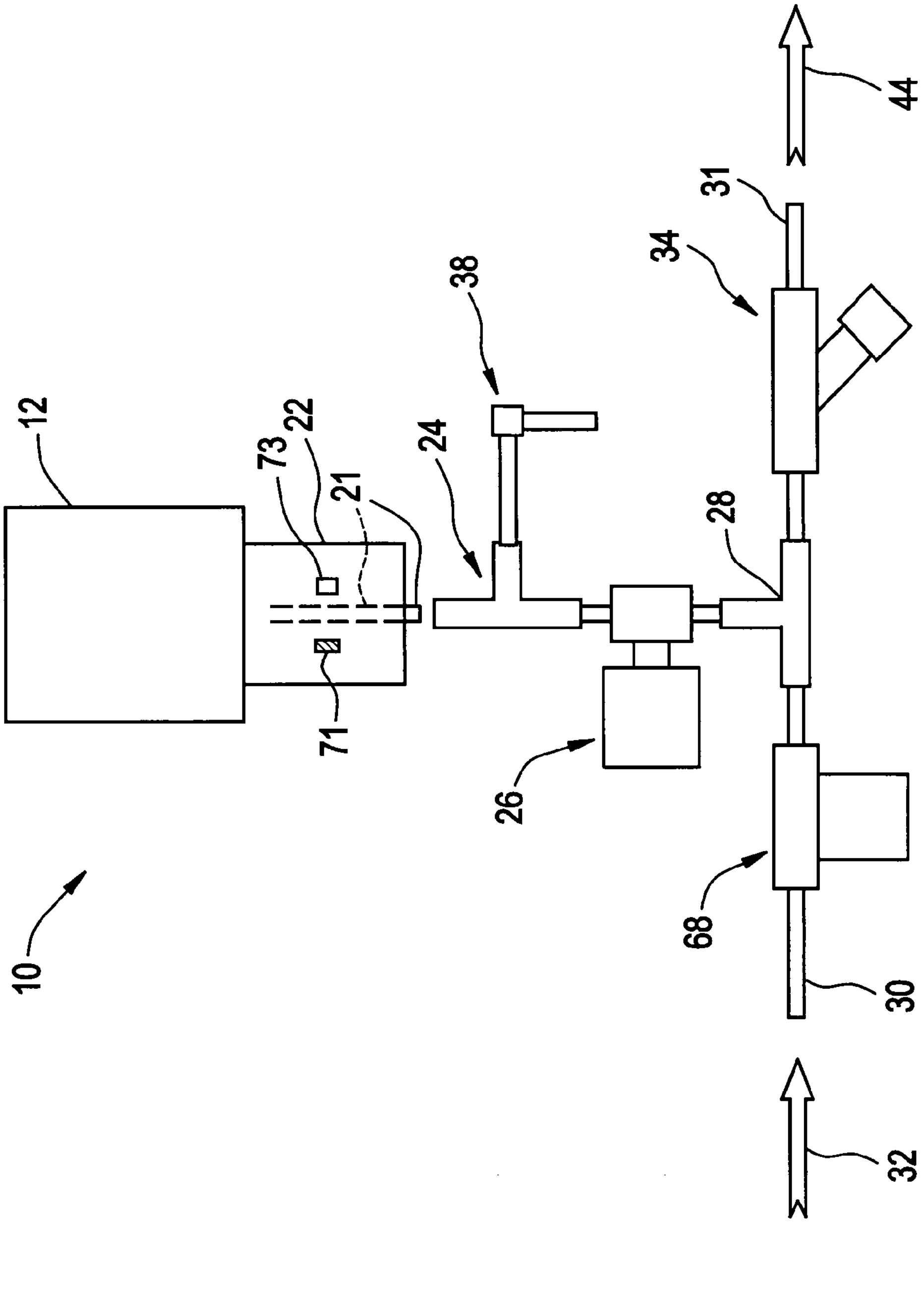
FIG. 1 is a view of the entire pellet feeder system and pipelines showing one possible configuration of all of the elements of the system.

The system of equipment 10 for feeding solid materials to a pressurized pipeline, one embodiment of which is shown in FIG. 1, has been found useful for handling solid materials that are available in most types of round shapes, rather than solid material in the form of granules or powders. For purposes of this patent application, the word "pellet" and the phrase "solid material" are to be taken to mean the same thing. Pellets can have many shapes, though oftentimes they are rounded or spherical or use some combination of round and straight geometry, such as a cylinder with rounded ends. For use with the system of this equipment, the pellets may be, but do not have to be, rounded or spherical or cylindrically shaped with rounded ends. The preferred pellets for an application involving the addition of resazurin to water have a cylindrical body and rounded ends. The pellets 36 can be anywhere from about 1/16 inch (about 0.2 cm) to about 5 inches (about 13 cm) in diameter with the preferred pellets being about 7/16 of an inch (about 1 cm) in diameter.

Pipe used in the system can be made of any suitable material of construction for industrial pipe from rigid metal or plastic pipe to flexible plastic or rubber hose. The preferred configuration is a rigid metal or plastic pipe. Suitable metal pipes include pipes made out of stainless steel, brass, copper, aluminum, steel, galvanized and black pipe. Suitable plastic pipes include EPDM (ethylene-propylene-diene-methylene) copolymer, PVC (polyvinyl chloride), CPVC (chlorinated polyvinyl chloride), polypropylene, PVDF (polyvinylidene fluoride), TFE (tetrafluoroethylene) and TFE PFA (tetrafluoroethylene perfluoroalkoxy). The preferred material for the pipes used in this system of equipment is PVC. PVC pipe is available commercially from many different sources including Ryan-Herco Inc., 1155 Frontenac Rd., Naperville Ill. 60563, (630)369-1141.

The solid material storage container 12 can be any commercially available container that meets the requirements for holding and dispensing the solid material of choice. It also can be fashioned out of available materials, such as PVC pipe that has had a top lid fastened at one end of the pipe and a means for delivering the pellets to the solid material pellet feeder attached to the bottom end of the pipe. One suitable means for delivering pellets 36 to solid material feeder 22, and from there to solid material feeder pipe 24, is a rotating plate (not shown) with holes in it, wherein the plate rotates a certain number of holes at a time in response to instructions relayed either manually or by using some sort of mechanical or electronic controller. The plate would be located at the bottom end of solid material storage container 12 and it would be aligned such that each pellet 36 would drop through transparent exit tube 21, the outline and visible end of which are shown in FIG. 1.

A suitable solid material storage container 12 that has been found useful when solid material 36 is sensitive to moisture has the following properties:

Color: Gray enclosure, clear polycarbonate transparent cover

Material: PVC with polycarbonate cover

Corrosion Resistance: $H_2O$, salt water, "salt air"

UV Resistance: Withstands exposure to direct sunlight

Desiccant holder: Included to hold one or more packs of desiccant close to the solid material. The desiccant holder is made out of a suitable material of construction such as stainless steel and is positioned on the inside of the cover to solid material storage container 12. Standard commercial available packets of desiccant can be inserted in the holder to remove moisture from the atmosphere around the pellets in the hopper. The use of a desiccant holder is optional, but it is recommended for pellets sensitive to moisture.

Ambient Operating Temperature: from about 4° C. to about 49° C. (from about 40° F. to about 120° F.)

Humidity: 5-100% non-condensing

Requires gravity equal to normal gravity on the terrestrial planets.

Suitable solid material storage containers are available from suppliers such as Ryan-Herco Inc., 1155 Frontenac Rd., Naperville Ill. 60563, (630)369-1141 and United States Plastic Corporation, 1390 Neubrecht Road, Lima, Ohio 45801-3196, (800)854-5498.

Solid material feeder 22 is affixed to solid material storage container 12 using any standard fastening technique. An alternative to having a separate solid material feeder, is to use a solid material feeder that is the bottom boundary of the solid material storage container 12.

The functionality of solid material feeder 22 is such that it must be capable of controlling the rate of allowing solid material 36 to pass from solid material storage container 12 into solid material feeder pipe 24 on its way to solid material transfer device 26. See Perry's Chemical Engineering Handbook, 7*th* Edition, McGraw Hill, for a discussion of solid materials containers and feeders and for information to aid a person of ordinary skill in the art to select and install a solid material storage container and a solid material feeder.

Pellets 36 leave solid material feeder 22 and enter solid material feeder pipe 24 which conveys each pellet 36 to solid material transfer device 26. Pipe suitable for solid material feeder pipe 24 is any commercially available pipe. A list of suitable pipe has been included previously in this text. The preferred pipe is PVC schedule 80 pipe, solvent welded where possible, capable of withstanding a maximum pressure of 75 psi @ 140° F. (60° C.) and 100 psi @ 100° F. (38° C.), Located on solid material feeder pipe 24, somewhere between the bottom of solid material feeder 22 and the top of solid material transfer device 26, there is horizontal drain pipe 38 (also known as a "horizontal tee" or "overflow tee" or "overflow hose" or even just "hose"). Horizontal drain pipe 38 is configured such that should any fluid 32 from pressurized process pipeline 30 get past solid material transfer device 26 into solid material feeder pipe 24, it will drain through horizontal drain pipe 38, before reaching solid material feeder 22.

Suitable materials for horizontal drain pipe 38, are any rigid or flexible pipe. The preferred pipe for horizontal drain pipe 38 is rigid PVC pipe. There is a 5" length of ¾" pipe welded to side of the tee. This is connected to a 90 degree elbow with a ¾" NPT (national pipe thread) to ½" hose adapter for connection to a drain.

In one embodiment, the top of solid material feeder pipe 24 has a 2 and ¾" length of ¾" pipe with Schedule 40 clear PVC coupling (non-welded). This clear PVC pipe, not shown in any of the drawings, is optional. It is present to facilitate inspection and maintenance of exit tube 21.

Pellets 36 travel down solid material feeder pipe 24 until they enter solid material transfer device 26. A cutaway view of one embodiment of solid material transfer device 26 is shown in FIGS. 4, 5, 6 and 7.

In FIGS. 4, 5, 6 and 7, motor housing 52 covers gear motor 50, which is used to operate coupler shaft 54, which works to invert rotating dispensing ball 62. Positional sensor 56 is used to orient rotating dispensing ball 62.

Solid material storage container 12 and solid material feeder 22 are configured and operated in such a way as to ensure that the correct amount of pellets are fed, based on an "order input". The order input can either be manual, mechanical operation of the solid material feeder (push a button, one pellet falls) or it can be of sophisticated operation such as accepting an electronic signal from a controller which is monitoring all aspects of an industrial water system, including the need for more of the solid material to be added to the pressurized pipeline.

Either at the bottom of solid material storage container 12 or at the top of solid material feeder 22 there is a motorized rotor (not shown in any of the figures) that rotates a plate, with one or more holes in it, which acts to select one pellet to be delivered through exit tube 21. Exit tube 21 must be transparent because the action of the pellet moving through exit tube 21 breaks the path of light emitted on one side of exit tube 21 by a suitable light source, such as light emitting diode 71. This interruption in the path of light is detected on the other side of exit tube 21 by any suitable detector, such as a photodiode 73. Both light emitting diode 71 and photodiode 73 are located in solid material feeder 22 as shown in FIG. 1. When photodiode 73 detects the break in the path of light, it waits a predetermined length of time and then sends a signal to solid material transfer device 26 to invert rotating dispensing ball 62.

Figure 4:
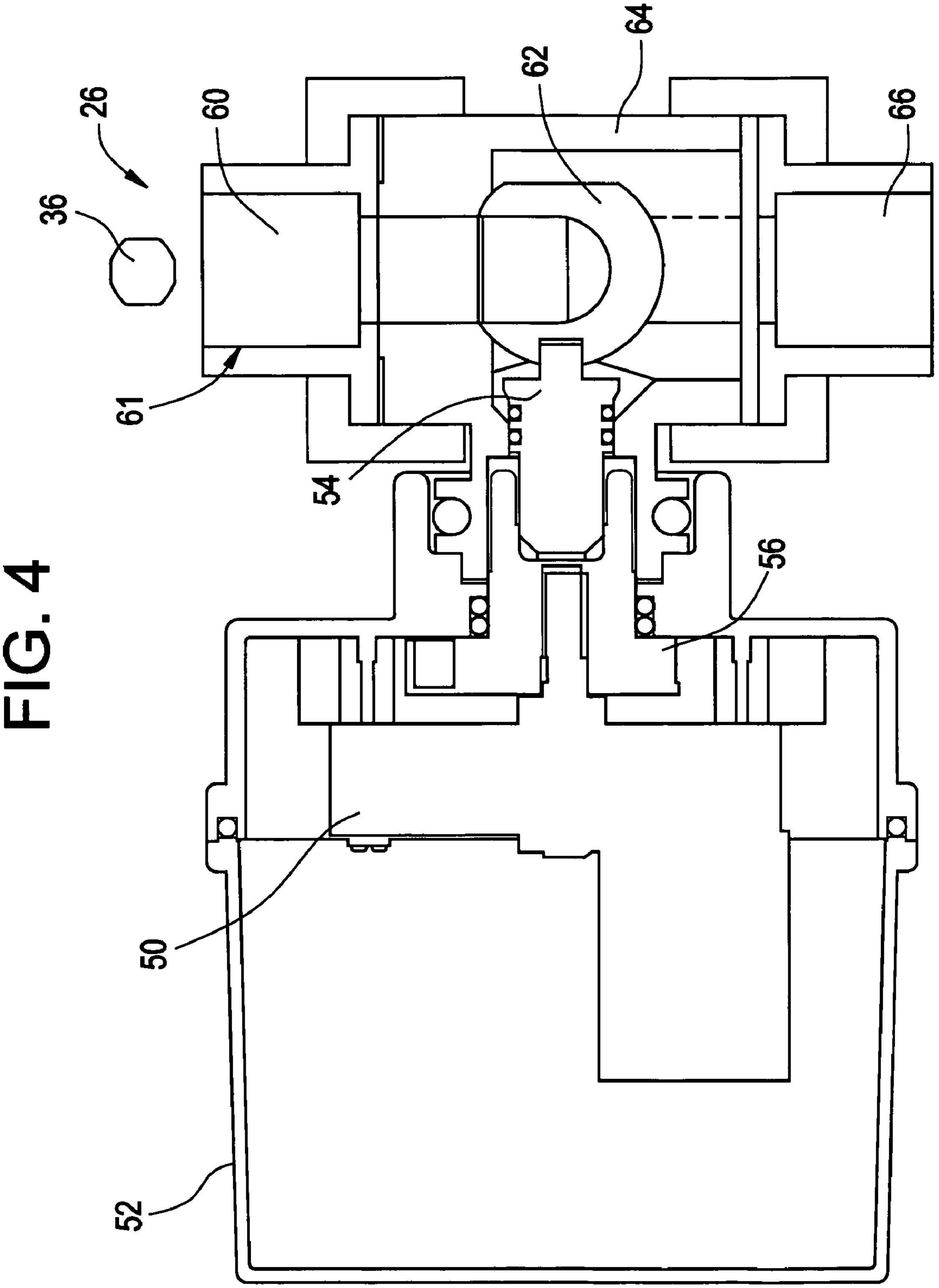
FIG. 4 is a cut-away view of a solid material transfer device showing a solid material about to enter the device from the top.

In FIG. 4, pellet 36 enters solid material injection device 26 at non-pressurized inlet 61, which is at the top 60 of rotating dispensing ball 62.

Figure 5:
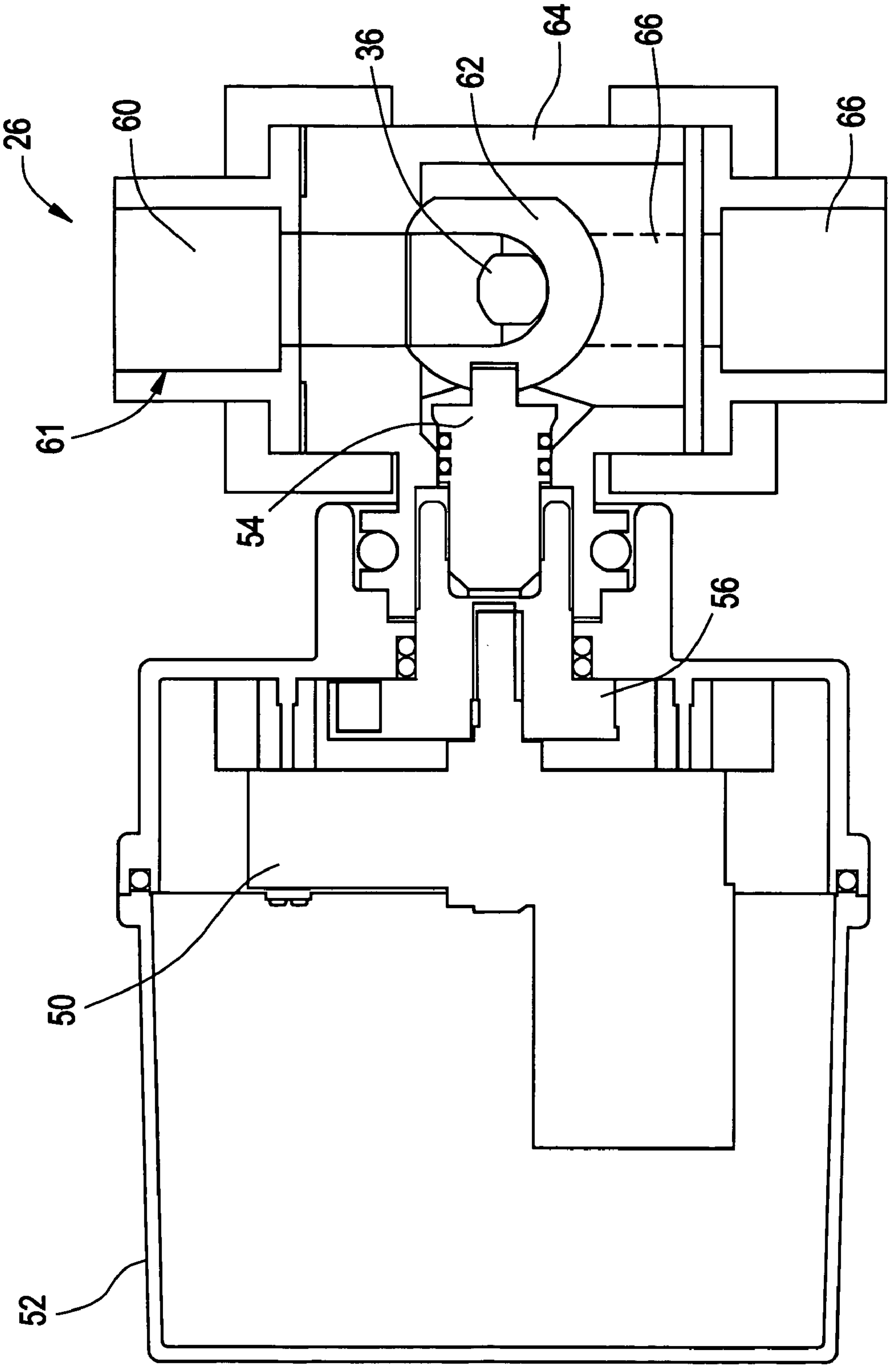
FIG. 5 is a cut-away view of a solid material transfer device showing a solid material at the tip of the rotating dispensing ball, wherein the rotating dispensing ball's open end is oriented upwards towards the solid material feeder pipe.

In FIG. 5, pellet 36 is shown at the tip of rotating dispensing ball 62. When solid material injection device 26 receives the signal from photodiode 73 it inverts rotating dispensing ball 62 in valve housing 64.

Figure 6:
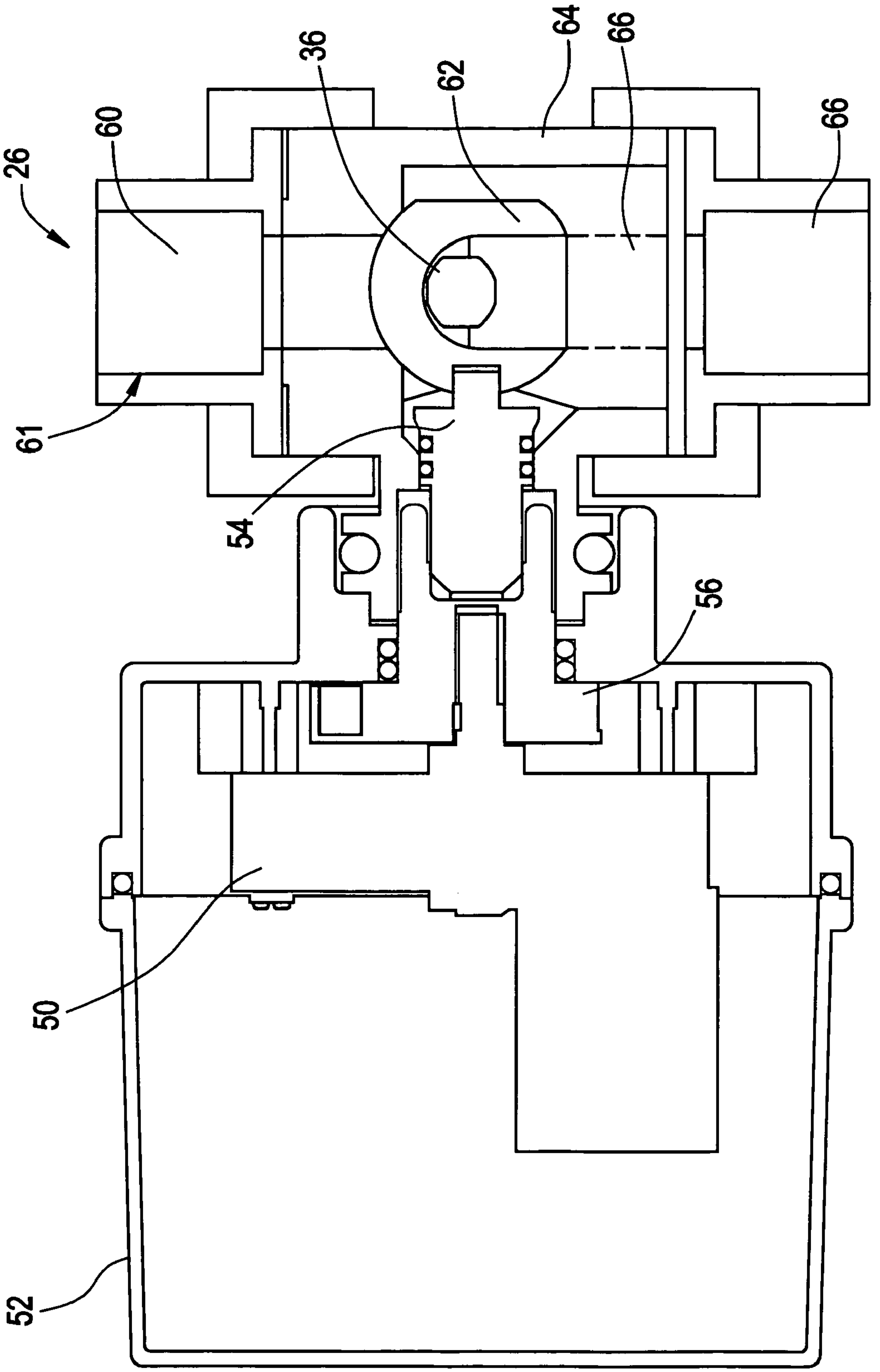
FIG. 6 is a cut-away view of a solid material transfer device showing a solid material at the tip of the rotating dispensing ball, wherein the rotating dispensing ball's open end is oriented downwards towards the point of intake in the process pipeline.

In FIG. 6, solid pellet 36 is shown at the tip of rotating dispensing ball 62 where rotating dispensing ball 62 is now inverted so that the opening is directed down through pressurized outlet 66.

Figure 7:
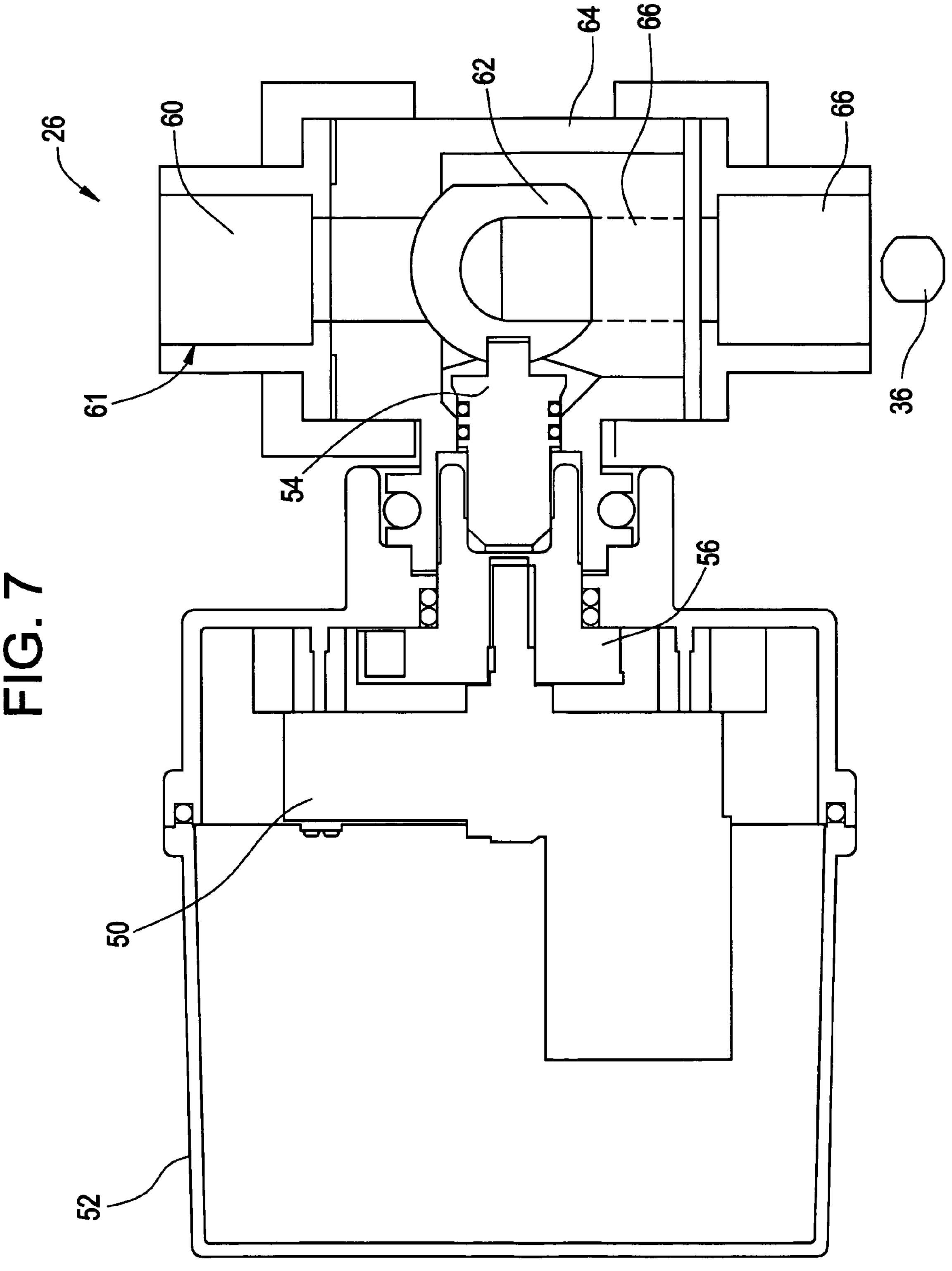
FIG. 7 is a cut-away view of a solid material leaving the solid material transfer device and entering the point of intake in the process pipeline.

In FIG. 7, pellet 36 is shown leaving solid material transfer device 26 at the bottom of pressurized outlet 66.

Use of solid material transfer device 26 enables the feeding of pellets 36 into a pressurized line, without leaks. Solid material transfer device 26 could be any transfer device with the following characteristics:

- Capable of feeding solid into pressurized line without leaks.
- Has a rotating collecting/dispensing ball inside a stationary casing or housing, where the ball can be operated by a motor. This motor is activated either manually or by receipt of a signal from a photodiode which detects the falling of each pellet.
- Inlet and outlet openings are circular and diametrically opposed.
- Opening diameters are preferably equal to the diameter of the hole in the ball.
- Filling and emptying action using gravity.
- Gaskets are around rotating dispensing ball and openings for sealing.

A suitable housing is available from Hayward Industrial Products, Inc., One Hayward Industrial Drive, Clemmons, N.C. 27012, 1-888-429-4635. The other components of the solid material transfer device can be made to order using a commercial machine shop.

The means for holding solid material in place for a sufficient length of time such that the liquid in said process pipeline can contact and dissolve said solid material downstream of the point of intake in the process pipeline is shown in FIG. 1 as Y-strainer 34. Two different embodiments of Y-strainer 34 are shown in FIGS. 2 and 3.

Figure 2:
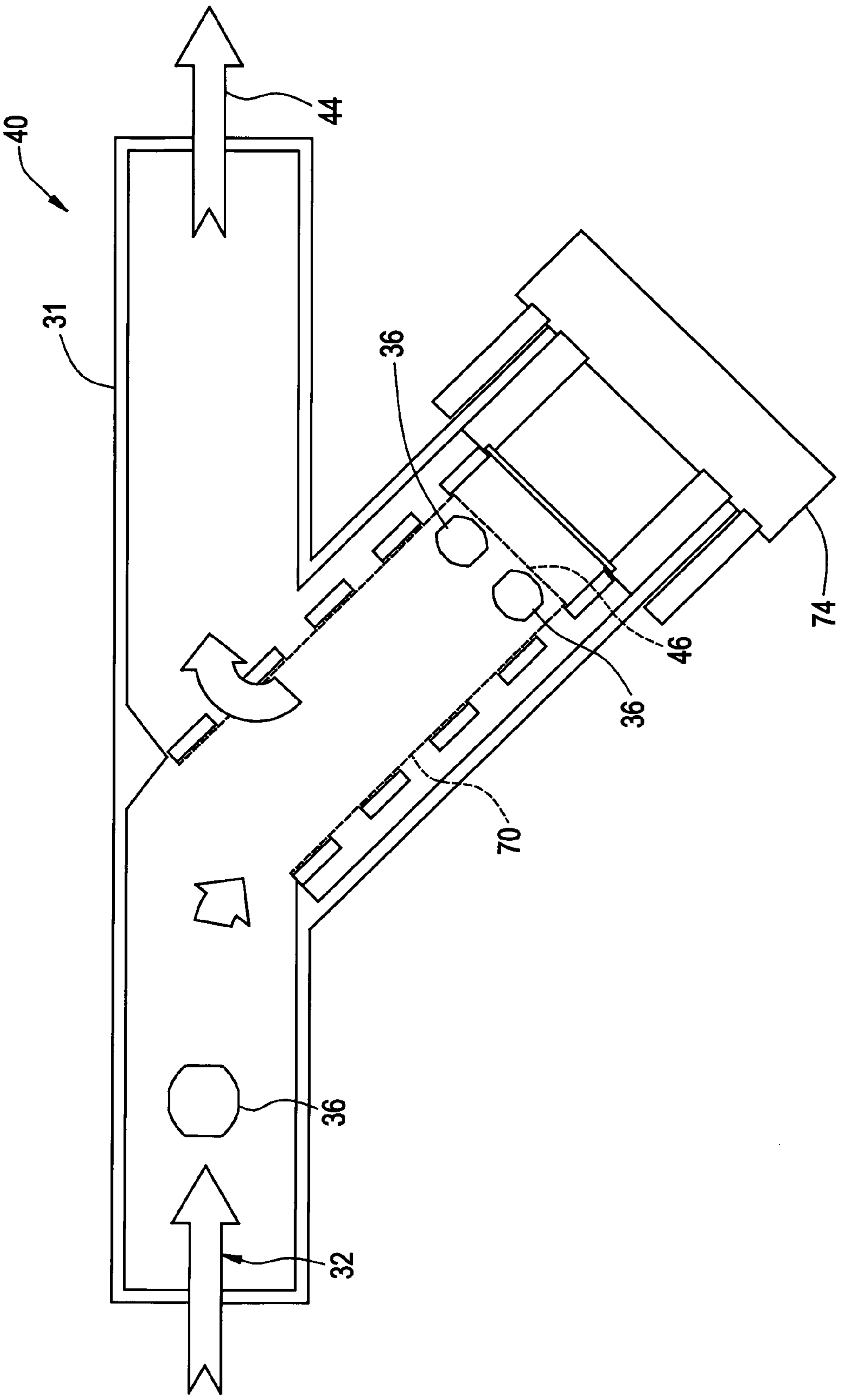
FIG. 2 is a cut-away view of the first embodiment of the Means for holding said solid material in place Element.

In FIG. 2, First Y-strainer 40 has a strainer basket 70 which permits the flow of liquid 32 while stopping solids with a specific diameter. Because of the flow patterns of liquid 32 in Y-strainer 40, the bottom screen 46 of First Y-strainer 40 is where pellets 36 collect. In FIG. 2 pellets 36 are shown resting on bottom screen 46 as they are dissolved by the flow of liquid 32. Downstream liquid 44 contains dissolved solid material as it travels onward through process pipe 31 which continues downstream of First Y-strainer 40. First Y-strainer 40 may be cleaned by unfastening bottom 74 and removing strainer basket 70.

Figure 3:
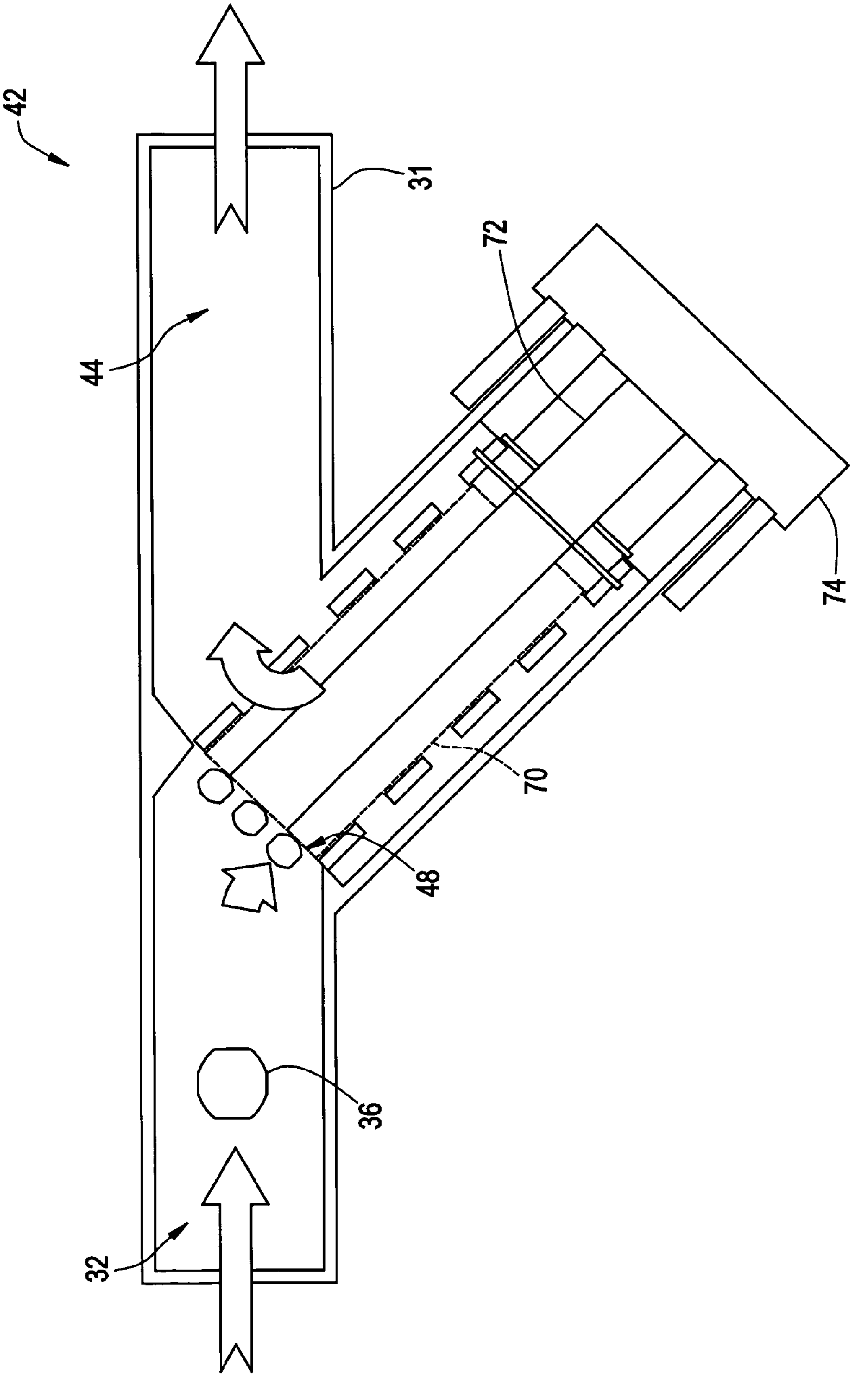
FIG. 3 is a cut-away view of the second embodiment of the Means for holding said solid material in place Element.

In FIG. 3, Second Y-strainer 42 has a strainer basket 70 which permits the flow of liquid 32 while stopping solids with a specific diameter. Second Y-strainer 42 has rod 72 positioned in the center of strainer basket 70. Rod 72 is affixed to bottom 74. Because of the flow patterns of liquid 32 in Second Y-strainer 42, the top 48 of rod 72 is where pellets 36 collect. After liquid 32 dissolves pellets 36, it travels onward through process pipe 31 as liquid 44, which continues downstream of Second Y-strainer 42.

In one working embodiment Y-strainer 42 is 6" long, with a ¾" inside diameter. Strainer basket 70 is 4" long and has a ¾" inside diameter. The longest side of the Y is 4⅜" long and is 1¼" inside diameter with a #20 mesh screen. Rod 72 has a ½" diameter and is 3⅞" long.

The Y-strainers shown in FIGS. 1, 2 and 3 are shown with the Y-strainer angled downwards. It has been found that the invention can work with the Y-strainer in any orientation, however, the preferred orientation for one embodiment of the instant claimed invention is that of Y-strainer 40, without rod 72, with the Y angled upwards. A suitable Y-strainer for use in the instant claimed invention is constructed of clear PVC with 20 mesh screen and union fittings. Y-strainers are commercially available through McMaster-Carr Supply Company, P.O. Box 4355, Chicago, Ill. 60680-4355, (630)833-0300.

The system of equipment described and claimed herein is preferably attached to a backplate to facilitate installation, access, maintenance and removal. In one embodiment of the instant claimed invention the backplate is a 2 ft by 2 ft by ⅜" thick PVC backplate with two machined PVC hardware mounts for the feeder, and three PVC mounts for the plumbing with stainless steel hardware.

An optional part of this system includes basket strainer 68 which, if present, is located upstream of point 28, where pellets 36 enter process pipeline 30. When basket strainer 68 is present, the size of the holes in the screen in basket strainer 68 are selected to be smaller than the holes in the screen in the Y-strainer.

The instant claimed invention has been found to be particularly useful in practicing the method described and claimed in U.S. Pat. No. 6,329,165, MEASUREMENT AND CONTROL OF SESSILE AND PLANKTONIC MICROBIOLOGICAL ACTIVITY IN INDUSTRIAL WATER SYSTEMS, which is hereby incorporated by reference, in its entirety.

When the solid material is resazurin, as is the preferred fluorogenic reagent in practicing the method of U.S. Pat. No. 6,329,165, it is preferred that the resazurin be formulated into a pellet using pelletizing ingredients known in the art. In addition to resazurin in the pellet, the other pelletizing ingredients may be selected from the group consisting of anhydrous sodium sulfate, HEDP(1-Hydroxyethylidene biphosphonate, Tetrasodium salt) and any suitable commercially available stearate material, including, but not limited to magnesium stearate, lithium stearate and calcium stearate. All of the ingredients in this pellet are commercially available from known chemical supply companies.

Pellets of resazurin, suitable for use with the system of equipment of the instant claimed invention, comprise a) from about 1 to about 40 weight percent resazurin;
b) from about 0 to about 30 weight percent anhydrous sodium sulfate;
c) from about 15 to about 60 weight percent 1-hydroxyethylidene biphosphonate, tetrasodium salt; and
d) from about 0.0 to about 4.0 weight percent stearate.

The preferred pellets of resazurin currently comprise:

a) from about 15 to about 25 weight percent resazurin;
b) from about 20 to about 30 weight percent anhydrous sodium sulfate;

c) from about 50 to about 60 weight percent 1-hydroxyethylidene biphosphonate, tetrasodium salt; and d) from about 0.3 to about 0.7 weight percent stearate.

The most preferred pellets of resazurin currently comprise:

a) about 20 weight percent resazurin;

b) about 25 weight percent anhydrous sodium sulfate;

c) about 54.5 weight percent 1-hydroxyethylidene biphosphonate, tetrasodium salt; and d) about 0.5 weight percent stearate, which is magnesium stearate.

When formulating these pellets it must be taken into account that resazurin is typically not available in a 100% actives form for use as a raw material. It is more typical to have resazurin available in a form of from about 75% to about 85% actives. All weight percentages of resazurin given in these formulations are as "active" resazurin.

The resazurin pellets are provided in a rounded form with approximately a 7/16" diameter. At present, the preferred pellet of resazurin is in the shape of a cylinder with rounded ends. The texture of the resazurin pellets is smooth to the touch. The pellets may be made using any standard pelletizing process.

In using the described and claimed system of equipment with resazurin pellets, it has been determined that, at the present time, the flow rate for dissolving the pellets in a reasonable length of time is from at least about 1 gallon per minute to at most about 200 gallons per minute, preferably from at least about 2 gallons per minute to at most about 50 gallons per minute, and most preferably from about 5 gallons per minute to at most about 10 gallons per minute.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A pellet comprising:

a) from about 1 to about 40 weight percent resazurin;

b) from about 0 to about 30 weight percent anhydrous sodium sulfate;

c) from about 15 to about 60 weight percent 1-hydroxyethylidene biphosphonate, tetrasodium salt; and d) from about 0.0 to about 4.0 weight percent stearate.

2. The pellet of claim 1 comprising:

a) from about 15 to about 25 weight percent resazurin;

b) from about 20 to about 30 weight percent anhydrous sodium sulfate;

c) from about 50 to about 60 weight percent 1-hydroxyethylidene biphosphonate, tetrasodium salt;

d) from about 0.3 to about 0.7 weight percent stearate.

3. The pellet of claim 1 comprising:

a) about 20 weight percent resazurin;

b) about 25 weight percent anhydrous sodium sulfate;

c) about 54.5 weight percent 1-hydroxyethylidene biphosphonate, tetrasodium salt; and d) about 0.5 weight percent stearate, which is magnesium stearate.

* * * * *